(12) United States Patent
Peng et al.

(10) Patent No.: US 11,604,132 B1
(45) Date of Patent: Mar. 14, 2023

(54) TESTING DEVICE AND EVALUATION METHOD FOR SENSITIVITY DAMAGE OF CORE PERMEABILITY TENSOR

(71) Applicant: Southwest Petroleum University, Chengdu (CN)

(72) Inventors: Yu Peng, Chengdu (CN); Yitao Huang, Chengdu (CN); Yongming Li, Chengdu (CN); Ang Luo, Chengdu (CN); Pengjun Shi, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 17/837,499

(22) Filed: Jun. 10, 2022

(30) Foreign Application Priority Data

Feb. 14, 2022 (CN) .......................... 202210131769.1

(51) Int. Cl.
*G01N 15/08* (2006.01)
*G01N 33/24* (2006.01)

(52) U.S. Cl.
CPC ................ *G01N 15/0826* (2013.01)

(58) Field of Classification Search
CPC .... G01N 15/00; G01N 15/08; G01N 15/0826; G01N 33/24
See application file for complete search history.

(56) References Cited

U.S. PATENT DOCUMENTS

| 10,302,798 | B2 * | 5/2019 | Benoit | ................. G01N 15/082 |
| 10,809,175 | B1 | 10/2020 | Ayadat | |
| 11,313,775 | B2 * | 4/2022 | Li | ........................... G01N 3/062 |

FOREIGN PATENT DOCUMENTS

| CN | 105067793 A | 11/2015 |
| CN | 106198338 A | 12/2016 |

(Continued)

OTHER PUBLICATIONS

Stress sensitivity anisotropy and its microscopic mechanism of tight oil and gas reservoirs: A case from the Chang-6 reservoir in Ansai oilfield of Ordos Basin. Zhiqiang Zhang et al. (Year: 2016).*

(Continued)

*Primary Examiner* — Nguyen Q. Ha
(74) *Attorney, Agent, or Firm* — Nitin Kaushik (57) ABSTRACT

The present invention discloses a testing device and evaluation method for sensitivity damage of core permeability tensor, comprising the following steps: first, obtain the cubic experimental rock samples and calculate the formation pressure distribution based on the reservoir geological data; then simulate the true stress and strain state of core in formation through triaxial stress loading, design the acid liquor, alkali liquor, inorganic salt solution, formation water and different displacement rates for displacement experiments, realize the determination of core three-directional permeability tensor under the same experimental conditions through three-directional sequential displacement, process the experimental data through Darcy's law, and calculate the damage degree of core permeability tensor under different sensitivity conditions of triaxial stress state; finally, identify the real-time flow state of fluid through permeability tensor synthesis, and realize the accurate and efficient testing and evaluation on permeability tensor sensitivity of reservoirs.

8 Claims, 2 Drawing Sheets

(56) References Cited

FOREIGN PATENT DOCUMENTS

| | | | |
|---|---|---|---|
| CN | 106522931 A | 3/2017 | |
| CN | 106769767 A | 5/2017 | |
| CN | 106845043 A | 6/2017 | |
| CN | 107764714 A * | 3/2018 | ........... G01N 15/082 |
| CN | 107764714 A | 3/2018 | |
| CN | 109238938 A | 1/2019 | |
| CN | 109557280 A | 4/2019 | |
| CN | 109580454 A | 4/2019 | |
| CN | 109653740 A | 4/2019 | |
| CN | 110566195 A | 12/2019 | |
| CN | 110617045 A | 12/2019 | |
| CN | 111006989 A | 4/2020 | |
| EP | 3493325 A1 | 6/2019 | |
| JP | 2013134143 A | 7/2013 | |
| WO | WO2012144976 A1 | 10/2012 | |
| WO | WO2017032520 A1 | 3/2017 | |

OTHER PUBLICATIONS

Experimental Study on the Effect of Coal Particle Size on the Mechanics, Pore Structure, and Permeability of Coal-like Materials for Low-Rank Coalbed Methane Reservoir Simulation. Yangfeng Zheng et al. (Year: 2021).*

* cited by examiner

TESTING DEVICE AND EVALUATION METHOD FOR SENSITIVITY DAMAGE OF CORE PERMEABILITY TENSOR

CROSS-REFERENCE TO RELATED APPLICATIONS

The application claims priority to Chinese patent application No. 202210131769.1, filed on Feb. 14, 2022, the entire contents of which are incorporated herein by reference.

TECHNICAL FIELD

The present invention relates to the technical field of oil and gas reservoir development, in particular to a testing device and evaluation method for sensitivity damage of core permeability tensor.

BACKGROUND

In recent years, with the rapid development of world economy, the increasing global demand for oil and gas and the dwindling of conventional oil and gas resources, unconventional oil and gas resources have become the main battlefield of current exploration and development. Its efficient development and utilization is of great significance for maintaining the stable economic growth and safeguarding the national energy security. In the development process of unconventional oil and gas resources, the more obvious physical and chemical reactions between the oil and gas reservoir and the external fluid will lead to changes in pore structure and permeability of reservoir, damage of reservoir permeability to different degrees, reduction in production output and loss in reserves. The sensitivity of reservoir permeability tensor includes rate sensitivity, water sensitivity, salt sensitivity, acid sensitivity, alkali sensitivity and stress sensitivity. Therefore, the change law and quantitative characterization of permeability tensor in different conditions are of great significance for the study on seepage law of reservoir fluid.

Currently, among the permeability testing and evaluation methods commonly used at home and abroad, after the cylindrical core is applied to load the corresponding formation pressure radially, the change value of reservoir permeability is determined by the change of axial displacement pressure difference, and then the damage degree of core permeability tensor is determined. But among the above methods, the pressure radially loaded by the core is equal, and there is no applied stress load in the direction of core displacement, which varies greatly from the actual stress load that the core bears in the formation. In addition, restricted by the core shape and the confining pressure loading mode, the traditional permeability determination method can only achieve the core permeability determination in one direction. In order to achieve the "three-directional" permeability determination, usually the cores need to be sampled in three directions for multiple measurements. Due to great differences between experimental conditions and actual formation conditions as well as tedious testing process and poor experimental economy, how to accurately and efficiently test the reservoir permeability tensor damage is still a major technical problem in the field of oil and gas development.

SUMMARY

In view of the above problems, the present invention aims to provide a testing device and evaluation method for sensitivity damage of core permeability tensor, which can achieve the efficient and accurate determination of three-directional core permeability tensor in the same experimental conditions.

The technical solution of the present invention is as follows:

On the one hand, a testing device for sensitivity damage of core permeability tensor is provided, comprising a core triaxial clamping system, a three-dimensional and three-directional displacement system, a back pressure system, a pressure monitoring system, a temperature simulation system, and a gas-liquid recovery system;

The core triaxial clamping system comprises six core clamping panels and three sets of pressure loading systems. The six core clamping panels are used to clamp the six sides of the cubic core, and the two adjacent core clamping panels are sealed by a seal assembly; each set of pressure loading system comprises two oil pumps, two hydraulic transmission rods, and a control system; the oil pump is connected with the hydraulic transmission rod, and the two hydraulic transmission rods of the same set of pressure loading system are respectively connected with the relative two core clamping panels, and the control system is used to control the two hydraulic transmission rods of the same set of pressure loading system to apply equal and opposite pressure loads on the two opposite end faces of the target core;

The three-dimensional and three-directional displacement system is connected with the core triaxial clamping system for three-dimensional and three-directional displacement of the cubic core; the back pressure system is connected to the core triaxial clamping system for applying back pressure to the cubic core; the pressure monitoring system is used to monitor the fluid pressure at the inlet end and outlet end of the cubic core, the back pressure at the outlet end of the cubic core, and the pressure load applied to the cubic core in each direction; the temperature simulation system is used to simulate the formation temperature conditions; and the gas-liquid recovery system is used to recover waste liquid and waste gas generated during the experiment.

Preferably, the center of the core clamping panel is provided with a fluid channel that runs through the core clamping panel, the inner surface of the core clamping panel is provided with a plurality of coaxial annular grooves with the center of the core clamping panel as the center, the annular grooves are connected through a linear groove, and the linear groove is connected with the fluid channel.

Preferably, a plurality of linear grooves are arranged, which are distributed in a ring array on the core clamping panel with the center of the core clamping panel as the center.

On the other hand, an evaluation method for sensitivity damage of core permeability tensor is also provided. The testing device for sensitivity damage of core permeability tensor described in either of the above items is used for evaluation, comprising the following steps:

S1: Collect the geological data about the target reservoir, obtain the stress distribution of target reservoir, and decompose the stress on the core into vertical stress $P_z$ and two horizontal stresses $P_x$ and $P_y$ orthogonal to the vertical stress;

S2: Obtain the target core of target reservoir, install it in the core triaxial clamping system after processing it into a cube, and test the connectivity and air tightness of the device after installation;

S3: Based on the three-directional displacement of the target core, carry out the sensitivity damage test, and record the pressure and flow data monitored in the displacement process in each direction; and the sensitivity damage test includes the acid sensitivity test, the alkali sensitivity test, the salt sensitivity test, the water sensitivity test, the rate sensitivity test or the stress sensitivity test, or in combination of them;

S4: Calculate the permeability value of the target core in each direction according to the pressure and flow data, and calculate the sensitivity damage rate in each direction according to the permeability value in each direction, where the direction corresponding to the maximum sensitivity damage rate is the direction having the strongest permeability sensitivity of target core.

Preferably, in the S3, when the acid sensitivity test is carried out, the target core is loaded with the corresponding applied stress according to the triaxial stress obtained in the S1, and then injected with the experimental acid liquor which is 0.5-1.5 times as much as the pore volume. The triaxial displacement is carried out after the target core reacts with the experimental acid liquor for 0.5 h;

When the alkali sensitivity test, the salt sensitivity test or the water sensitivity test is carried out, the target core is loaded with the corresponding applied stress according to the triaxial stress obtained in the S1, and then injected with the experimental fluid which is 10-15 times as much as the pore volume. The triaxial displacement is carried out after the target core reacts with the experimental acid liquor for 12 h.

Preferably, in the S3, when the rate sensitivity test is carried out, the target core is loaded with the corresponding applied stress according to the triaxial stress obtained in step S1. Different flow rates are set, and the triaxial displacement is carried out in the order of flow rate from small to large.

Preferably, in the S3, when the stress sensitivity test is carried out, the method comprises the following sub-steps:

S31: Set the variable step lengths $\Delta P_x$, $\Delta P_y$ and $\Delta P_z$ of pressure in each direction;

S32: Determine the applied stress of the first time step in each direction, and use the applied stress of the first time step for three-directional displacement;

S33: According to the variable step lengths of pressure set in the S31, successively carry out the three-directional displacement under the applied stresses of the second time step, the third time step, . . . and the time step i.

Preferably, in the S31, the variable step lengths of pressure in each direction are within the scope of 3-5 MPa.

Preferably, in the S32, the applied stress of the first time step in each direction is calculated according to the following equations:

$$P_{x1}=P_x-P_1 \quad (1)$$

$$P_{y1}=P_y-P_1 \quad (2)$$

$$P_{z1}=\rho gh-P_1 \quad (3)$$

Where, $P_{x1}$, $P_{y1}$ and $P_{z1}$ are respectively the effective formation stresses of the target core under the first time step in x, y and z directions; $P_x$ and $P_y$ are respectively the original formation stresses of the target core in x and y directions; $P_1$ is the original pore pressure of reservoir; $\rho$ is the rock density; g is the gravitational acceleration; and h is the buried depth of target core.

Preferably, in the S4, the permeability value in each direction is calculated according to the following equations:

$$K_{xi} = \frac{Q_{xi} \times \mu \times L}{A \times (P_{xi-in} - P_{xi-out})} \quad (4)$$

$$K_{yi} = \frac{Q_{yi} \times \mu \times L}{A \times (P_{yi-in} - P_{yi-out})} \quad (5)$$

$$K_{zi} = \frac{Q_{zi} \times \mu \times L}{A \times (P_{zi-in} - P_{zi-out})} \quad (6)$$

Where, $K_{xi}$, $K_{yi}$ and $K_{zi}$ are respectively the permeability of target core under the time step i in x, y and z directions; $Q_{xi}$, $Q_{yi}$ and $Q_{zi}$ are respectively the flow rates under the time step i in x, y and z directions; $\rho$ is the viscosity of displacement fluid; L is the length of target core; A is the cross sectional area of target core; $P_{xi-in}$, $P_{yi-in}$ and $P_{zi-in}$ are respectively the inlet pressure under the time step i in x, y and z directions; $P_{xi-out}$, $P_{yi-out}$ and $P_{zi-out}$ are respectively the outlet pressure under the time step i in x, y and z directions;

The sensitivity damage rate in each direction is calculated according to the following equations:

$$D_{x(i-1)} = \frac{K_{x1} - K_{xi}}{K_{x1}} \times 100\% \quad (7)$$

$$D_{y(i-1)} = \frac{K_{y1} - K_{yi}}{K_{y1}} \times 100\% \quad (8)$$

$$D_{z(i-1)} = \frac{K_{z1} - K_{zi}}{K_{z1}} \times 100\% \quad (9)$$

Where, $D_{x(i-1)}$, $D_{y(i-1)}$ and $D_{z(i-1)}$ are respectively the sensitivity damage rates of target core in x, y and z directions after the time step 1 changes into the time step i;

The maximum sensitivity damage rates in each direction are calculated according to the following equations:

$$D_{xmax}=\max(D_{x1},D_{x2},\ldots D_{x(n-1)}) \quad (10)$$

$$D_{ymax}=\max(D_{y1},D_{y2},\ldots D_{y(n-1)}) \quad (11)$$

$$D_{zmax}=\max(D_{z1},D_{z2},\ldots D_{z(n-1)}) \quad (12)$$

Where, $D_{xmax}$, $D_{ymax}$ and $D_{zmax}$ are respectively the maximum sensitivity damage rates in x, y and z directions; $D_{x1}$, $D_{x2}$ and $D_{x(n-1)}$ are respectively the sensitivity damage rates in x direction after the time step 1 changes into the time step 2, into the time step 3 and into the time step n; $D_{y1}$, $D_{y2}$ and $D_{y(n-1)}$ are respectively the sensitivity damage rates in y direction after the time step 1 changes into the time step 2, into the time step 3 and into the time step n; $D_{z1}$, $D_{z2}$ and $D_{z(n-1)}$ are respectively the sensitivity damage rates in z direction after the time step 1 changes into the time step 2, into the time step 3 and into the time step n;

The beneficial effects of the present invention are as follows:

The present invention can realize the triaxial loading of real ground stress on the target core through the core triaxial clamping system, and can ensure the authenticity and accuracy of the core permeability tensor damage test to the greatest extent by simulating the real stress and stress change process of the core in the reservoir. The present invention, featured by simple operation of device and experimental method, can realize the three-directional permeability test of core in an experiment, greatly increasing the convenience of core permeability test. Moreover, one device can be used for multiple purposes. The three-directional sensitivity damage test of reservoir permeability, including the acid sensitivity, the alkali sensitivity, the salt sensitivity, the water sensitivity, the rate sensitivity and the stress sensitivity, can be realized. The test items are more comprehensive, and the evaluation criteria are more diverse and accurate.

BRIEF DESCRIPTION OF DRAWINGS

In order to explain the embodiments of the present invention or the technical solutions in the prior art more clearly, the following will make a brief introduction to the drawings needed in the description of the embodiments or the prior art. Obviously, the drawings in the following description are merely some embodiments of the present invention. For those of ordinary skill in the art, other drawings can be obtained based on the structures shown in these drawings without any creative effort.

DETAILED DESCRIPTION OF THE EMBODIMENTS

The present invention is further described with reference to the drawings and embodiments. It should be noted that the embodiments in this application and the technical features in the embodiments can be combined with each other without conflict. It is to be noted that, unless otherwise specified, all technical and scientific terms herein have the same meaning as commonly understood by those of ordinary skill in the art to which this application belongs. "Include" or "comprise" and other similar words used in the present disclosure mean that the components or objects before the word cover the components or objects listed after the word and its equivalents, but do not exclude other components or objects.

Figure 1:
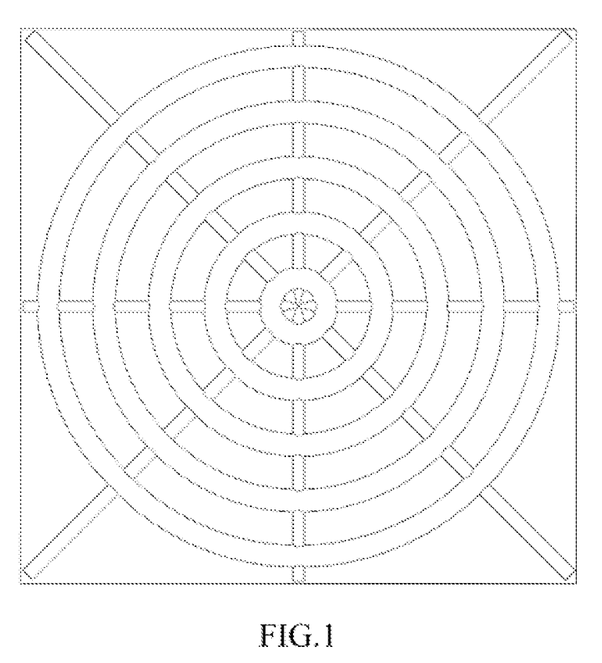
FIG. 1 is the structure diagram of core clamping panel of the testing device for sensitivity damage of core permeability tensor in the present invention.
Figure 2:
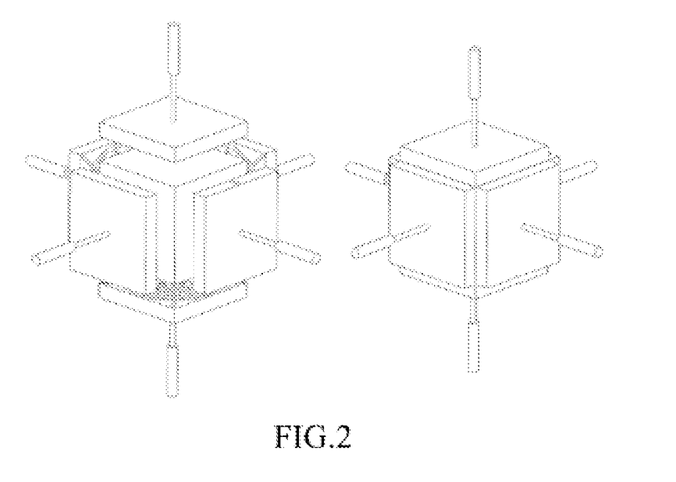
FIG. 2 is the installation status structure diagram of core clamping panel of the testing device for sensitivity damage of core permeability tensor in the present invention.

On the one hand, as shown in FIG. 1-2, the present invention provides a testing device for sensitivity damage of core permeability tensor, comprising a core triaxial clamping system, a three-dimensional and three-directional displacement system, a back pressure system, a pressure monitoring system, a temperature simulation system, and a gas-liquid recovery system;

The core triaxial clamping system comprises six core clamping panels and three sets of pressure loading systems. The six core clamping panels are used to clamp the six sides of the cubic core, and the two adjacent core clamping panels are sealed by a seal assembly; each set of pressure loading system comprises two oil pumps, two hydraulic transmission rods, and a control system; the oil pump is connected with the hydraulic transmission rod, and the two hydraulic transmission rods of the same set of pressure loading system are respectively connected with the relative two core clamping panels, and the control system is used to control the two hydraulic transmission rods of the same set of pressure loading system to apply equal and opposite pressure loads on the two opposite end faces of the target core;

The three-dimensional and three-directional displacement system is connected with the core triaxial clamping system for three-dimensional and three-directional displacement of the cubic core; the back pressure system is connected to the core triaxial clamping system for applying back pressure to the cubic core; the pressure monitoring system is used to monitor the fluid pressure at the inlet end and outlet end of the cubic core, the back pressure at the outlet end of the cubic core, and the pressure load applied to the cubic core in each direction; the temperature simulation system is used to simulate the formation temperature conditions; and the gas-liquid recovery system is used to recover waste liquid and waste gas generated during the experiment;

In order to reduce the fluid end effect, optionally, the center of the core clamping panel is provided with a fluid channel that runs through the core clamping panel, the inner surface of the core clamping panel is provided with a plurality of coaxial annular grooves with the center of the core clamping panel as the center, the annular grooves are connected through a linear groove, and the linear groove is connected with the fluid channel; a plurality of linear grooves are arranged, which are distributed in a ring array on the core clamping panel with the center of the core clamping panel as the center.

In a specific embodiment, the three-dimensional and three-directional displacement system comprises a 2PB constant flux pump, a high-pressure gas source, an intermediate container, a high-temperature and high-pressure pipeline, and the core clamping panel. The three-dimensional and three-directional displacement system connects the 2PB constant flux pump to the core clamping panels in three different directions. A valve bank is used to control the displacement direction of fluid, mainly for providing a constant flow rate of fluid in different directions when testing the permeability tensor damage. The high-pressure gas source is used to provide gas at a stable flow rate for gas permeability measurement. The intermediate containers are used to hold different types of experimental fluids (acid, alkali, salt, etc.) for core sensitivity testing in triaxial and three-directional reservoir, and the high-temperature and high-pressure pipeline can be used to connect all parts of the experimental device in the displacement system.

The back pressure system comprises a back-pressure valve and a 2PB constant flux pump (or hand pump). When the pressure of displacement system needs to be increased, the back-pressure valve is connected with the outlet end of displacement system and then connected with the constant flux pump (or hand pump) via the high-temperature and high-pressure pipeline. Here the 2PB constant flux pump (or hand pump) provides the back pressure for outlet end.

The pressure monitoring system comprises a plurality of pressure sensors, which is used for monitoring the fluid pressure at the inlet end and outlet end of target core, the back pressure at the outlet end of target core as well as the applied pressure load on target core in each direction.

The high and low temperature constant temperature system comprises a full-automatic high and low temperature constant temperature experimental box that can set different experimental temperatures according to the experimental requirements and simulate the temperature conditions in formation.

The gas-liquid recovery system comprises a waste liquid cylinder, a gas-liquid separator and a gas recovery bag. The gas-liquid recovery system is used to recycle the waste liquid and waste gas generated in the experiment process to avoid environmental pollution.

On the other hand, the present invention further provides an evaluation method for sensitivity damage of core permeability tensor, and the testing device for sensitivity damage of core permeability tensor described in either of the above items is used for evaluation.

In a specific embodiment, the evaluation of acid sensitivity comprises the following steps:

(1) Collect the geological data about the target reservoir, determine the stress distribution of reservoir according to seismic interpretation, logging information, ground stress test data and other related data, and decompose the stress on target core into the vertical stress $P_z$ and two horizontal stresses $P_x$ and $P_y$ orthogonal to the vertical stress;

(2) Obtain the target core of target reservoir, and install it in the core triaxial clamping system after processing it into a cube; preferably, process the target core as per the dimension of 5 cm×5 cm×5 cm, and pay attention to the flatness of each end face during processing so as to load the applied stress to each end face of rock sample uniformly and avoid stress concentration;

(3) Inspect the connectivity and air tightness of the remaining parts of the testing device for sensitivity damage of core permeability tensor, and then enter the next step;

(4) Place the target rock sample on the core clamping panel at the lower part of z axis, operate the pressure loading control system to fix the target core on the core clamping panel, and then load the corresponding applied stresses in different directions according to the three-directional stresses $P_x$, $P_y$ and $P_z$ obtained in Step (1);

(5) According to different external fluids, different types of formation minerals, and different mineralization degrees of formation fluids, reasonably set the concentration of experimental acid solution, inject the experimental acid solution that is 0.5-1.5 times as much as the pore volume into the target core according to the type of rock sample, stop displacement and close the inlet and outlet of core triaxial clamping system, carry out three-directional displacement in sequence after the target rock sample reacts with the experimental fluid for 0.5 h, record the experimental monitoring data, and calculate the permeability value of target core in each direction:

$$K_{xi} = \frac{Q_{xi} \times \mu \times L}{A \times (P_{xi-in} - P_{xi-out})} \quad (4)$$

$$K_{yi} = \frac{Q_{yi} \times \mu \times L}{A \times (P_{yi-in} - P_{yi-out})} \quad (5)$$

$$K_{zi} = \frac{Q_{zi} \times \mu \times L}{A \times (P_{zi-in} - P_{zi-out})} \quad (6)$$

Where, $K_{xi}$, $K_{yi}$ and $K_{zi}$ are respectively the permeability of target core under the time step i in x, y and z directions; $Q_{xi}$, $Q_{yi}$ and $Q_{zi}$ are respectively the flow rates under the time step i in x, y and z directions; $\rho$ is the viscosity of displacement fluid; L is the length of target core; A is the cross sectional area of target core; $P_{xi-in}$, $P_{yi-in}$ and $P_{zi-in}$ are respectively the inlet pressure under the time step i in x, y and z directions; $P_{xi-out}$, $P_{yi-out}$ and $P_{zi-out}$ are respectively the outlet pressure under the time step i in x, y and z directions;

(6) According to the permeability value in each direction, calculate the three-directional sensitivity damage rate of target core under the applied triaxial stress conditions as well as the maximum acid sensitivity damage rate of three-directional permeability for target core in the experiments with different acid concentrations, in which the direction having the maximum damage rate of core permeability is that having the strongest acid sensitivity of core permeability;

$$D_{x(i-1)} = \frac{K_{x1} - K_{xi}}{K_{x1}} \times 100\% \quad (7)$$

$$D_{y(i-1)} = \frac{K_{y1} - K_{yi}}{K_{y1}} \times 100\% \quad (8)$$

$$D_{z(i-1)} = \frac{K_{z1} - K_{zi}}{K_{z1}} \times 100\% \quad (9)$$

$$D_{xmax} = \max(D_{x1}, D_{x2}, \ldots D_{x(n-1)}) \quad (10)$$

$$D_{ymax} = \max(D_{y1}, D_{y2}, \ldots D_{y(n-1)}) \quad (11)$$

$$D_{zmax} = \max(D_{z1}, D_{z2}, \ldots D_{z(n-1)}) \quad (12)$$

Where, $D_{x(i-1)}$, $D_{y(i-1)}$ and $D_{z(i-1)}$ are respectively the sensitivity damage rates of target core in x, y and z directions after the time step 1 changes into the time step i; $D_{xmax}$, $D_{ymax}$ and $D_{zmax}$ are respectively the maximum sensitivity damage rates in x, y and z directions; $D_{x1}$, $D_{x2}$ and $D_{x(n-1)}$ are respectively the sensitivity damage rates in x direction after the time step 1 changes into the time step 2, into the time step 3 and into the time step n; $D_{y1}$, $D_{y2}$ and $D_{y(n-1)}$ are respectively the sensitivity damage rates in y direction after the time step 1 changes into the time step 2, into the time step 3 and into the time step n; $D_{z1}$, $D_{z2}$ and $D_{z(n-1)}$ are respectively the sensitivity damage rates in z direction after the time step 1 changes into the time step 2, into the time step 3 and into the time step n;

In a specific embodiment, the evaluation of alkali sensitivity comprises the following steps:

(1) Collect the geological data about the target reservoir, determine the stress distribution of reservoir according to seismic interpretation, logging information, ground stress test data and other related data, and decompose the stress on target core into the vertical stress $P_z$ and two horizontal stresses $P_x$ and $P_y$ orthogonal to the vertical stress;

(2) Obtain the target core of target reservoir, and install it in the core triaxial clamping system after processing it into a cube; preferably, process the target core as per the dimension of 5 cm×5 cm×5 cm, and pay attention to the flatness of each end face during processing so as to load the applied stress to each end face of rock sample uniformly and avoid stress concentration;

(3) Inspect the connectivity and air tightness of the remaining parts of the testing device for sensitivity damage of core permeability tensor, and then enter the next step;

(4) Place the target rock sample on the core clamping panel at the lower part of z axis, operate the pressure loading control system to fix the target core on the core clamping panel, and then load the corresponding applied stresses in different directions according to the three-directional stresses $P_x$, $P_y$ and $P_z$ obtained in Step (1);

(5) According to different external fluids, different types of formation minerals, and different mineralization degrees of formation fluids, reasonably set the concentration of experimental alkali solution, inject the experimental alkali solution that is 10-15 times as much as the pore volume into the target core according to the type of rock sample, stop displacement and close the inlet and outlet of core triaxial clamping system, carry out three-directional displacement in sequence after the target rock sample reacts with the experimental fluid for 12 h, record the experimental monitoring data, and calculate the permeability value of target core in each direction in combination with the Equations (4)-(6);

(6) According to the permeability value in each direction, calculate the three-directional sensitivity damage rate of target core under the applied triaxial stress conditions as well as the maximum alkali sensitivity damage rate of three-directional permeability for target core in the experiments with different alkali concentrations in combination with the Equations (7)-(12), in which the direction having the maximum damage rate of core permeability is that having the strongest alkali sensitivity of core permeability;

In a specific embodiment, the evaluation of salt sensitivity comprises the following steps:

(1) Collect the geological data about the target reservoir, determine the stress distribution of reservoir according to seismic interpretation, logging information, ground stress test data and other related data, and decompose the stress on target core into the vertical stress $P_z$ and two horizontal stresses $P_x$ and $P_y$ orthogonal to the vertical stress;

(2) Obtain the target core of target reservoir, and install it in the core triaxial clamping system after processing it into a cube; preferably, process the target core as per the dimension of 5 cm×5 cm×5 cm, and pay attention to the flatness of each end face during processing so as to load the applied stress to each end face of rock sample uniformly and avoid stress concentration;

(3) Inspect the connectivity and air tightness of the remaining parts of the testing device for sensitivity damage of core permeability tensor, and then enter the next step;

(4) Place the target rock sample on the core clamping panel at the lower part of z axis, operate the pressure loading control system to fix the target core on the core clamping panel, and then load the corresponding applied stresses in different directions according to the three-directional stresses $P_x$, $P_y$ and $P_z$ obtained in Step (1);

(5) According to different external fluids, different types of formation minerals, and different mineralization degrees of formation fluids, reasonably set the mineralization degree of experimental fluid, inject the experimental fluid that is 10-15 times as much as the pore volume into the target core according to the type of rock sample, stop displacement and close the inlet and outlet of core triaxial clamping system, carry out three-directional displacement in sequence after the target rock sample reacts with the experimental fluid for 12 h, record the experimental monitoring data, and calculate the permeability value of target core in each direction in combination with the Equations (4)-(6);

(6) According to the permeability value in each direction, calculate the three-directional sensitivity damage rate of target core under the applied triaxial stress conditions as well as the maximum salt sensitivity damage rate of three-directional permeability for target core in the experiments with different mineralization degrees of experimental fluid in combination with the Equations (7)-(12), in which the direction having the maximum damage rate of core permeability is that having the strongest salt sensitivity of core permeability;

In a specific embodiment, the evaluation of water sensitivity comprises the following steps:

(1) Collect the geological data about the target reservoir, determine the stress distribution of reservoir according to seismic interpretation, logging information, ground stress test data and other related data, and decompose the stress on target core into the vertical stress $P_z$ and two horizontal stresses $P_x$ and $P_y$ orthogonal to the vertical stress;

(2) Obtain the target core of target reservoir, and install it in the core triaxial clamping system after processing it into a cube; preferably, process the target core as per the dimension of 5 cm×5 cm×5 cm, and pay attention to the flatness of each end face during processing so as to load the applied stress to each end face of rock sample uniformly and avoid stress concentration;

(3) Inspect the connectivity and air tightness of the remaining parts of the testing device for sensitivity damage of core permeability tensor, and then enter the next step;

(4) Place the target rock sample on the core clamping panel at the lower part of z axis, operate the pressure loading control system to fix the target core on the core clamping panel, and then load the corresponding applied stresses in different directions according to the three-directional stresses $P_x$, $P_y$ and $P_z$ obtained in Step (1);

(5) Inject the distilled water that is 10-15 times as much as the pore volume into the target core, stop displacement and close the inlet and outlet of core triaxial clamping system, carry out three-directional displacement in sequence after the target rock sample reacts with the experimental fluid for 12 h, record the experimental monitoring data, and calculate the permeability value of target core in each direction in combination with the Equations (4)-(6);

(6) According to the permeability value in each direction, calculate the three-directional sensitivity damage rate of target core under the applied triaxial stress conditions as well as the maximum water sensitivity damage rate of three-directional permeability for target core in combination with the Equations (7)-(12), in which the direction having the maximum damage rate of core permeability is that having the strongest water sensitivity of core permeability;

In a specific embodiment, the evaluation of rate sensitivity comprises the following steps:

(1) Collect the geological data about the target reservoir, determine the stress distribution of reservoir according to seismic interpretation, logging information, ground stress test data and other related data, and decompose the stress on target core into the vertical stress $P_z$ and two horizontal stresses $P_x$ and $P_y$ orthogonal to the vertical stress;

(2) Obtain the target core of target reservoir, and install it in the core triaxial clamping system after processing it into a cube; preferably, process the target core as per the dimension of 5 cm×5 cm×5 cm, and pay attention to the flatness of each end face during processing so as to load the applied stress to each end face of rock sample uniformly and avoid stress concentration;

(3) Inspect the connectivity and air tightness of the remaining parts of the testing device for sensitivity damage of core permeability tensor and then enter the next step;

(4) Place the target rock sample on the core clamping panel at the lower part of z axis, operate the pressure loading control system to fix the target core on the core clamping panel, and then load the corresponding applied stresses in different directions according to the three-directional stresses $P_x$, $P_y$ and $P_z$ obtained in Step (1):

(5) Set different flow rates, and carry out three-directional displacement in an order of flow rate from small to large; preferably, carry out three-directional displacement in an order of flow rate (0.1 cm$^3$/min, 0.25 cm$^3$/min, 0.5 cm$^3$/min, 0.75 cm$^3$/min, 1 cm$^3$/min, 1.5 cm$^3$/min, 2 cm$^3$/min, 3 cm$^3$/min, 4 cm$^3$/min, 5 cm$^3$/min, 6 cm$^3$/min); record the experimental monitoring data, and calculate the permeability value of target core in each direction in combination with the Equations (4)-(6);

(6) According to the permeability value in each direction, calculate the three-directional sensitivity damage rate of target core in an experiment of different displacement rates under the applied triaxial stress conditions as well as the maximum rate sensitivity damage rate of three-directional permeability for target core, in which the direction having the maximum damage rate of core permeability is that having the strongest rate sensitivity of core permeability.

In a specific embodiment, the evaluation of stress sensitivity includes the following steps:

(1) Collect the geological data about the target reservoir, determine the stress distribution of reservoir according to seismic interpretation, logging information, ground stress test data and other related data, and decompose the stress on target core into the vertical stress $P_z$ and two horizontal stresses $P_x$ and $P_y$ orthogonal to the vertical stress;

(2) Set the variable step lengths $\Delta P_x$, $\Delta P_y$ and $\Delta P_z$ of pressure in each direction, and determine the applied stress of the first time step in each direction; to avoid causing plastic failure to the core due to too large step length of pressure, preferably, the value of variable step length shall be within the scope of 3-5 MPa; and the variable step length of pressure in each direction can be calculated according to the following equation:

$$\Delta P_x = \Delta P_y = \Delta P_z = \frac{P_1 - P_i}{N} \quad (13)$$

Where, $P_1$ is the original pore pressure of reservoir; $P_1$ is the pore pressure when the oil reservoir is abandoned; and N is the number of time steps;

The applied stress of the first time step in each direction is calculated according to the following equations:

$$P_{x1} = P_x - P_1 \quad (1)$$

$$P_{y1} = P_y - P_1 \quad (2)$$

$$P_{z1} = \rho g h - P_1 \quad (3)$$

Where, $P_{x1}$, $P_{y1}$ and $P_{z1}$ are respectively the effective formation stresses of the target core under the first time step in x, y and z directions; $P_x$ and $P_y$ are respectively the original formation stresses of the target core in x and y directions; $P_1$ is the original pore pressure of reservoir, $\rho$ is the rock density; g is the gravitational acceleration; and h is the buried depth of target core.

(3) Obtain the target core of target reservoir, and install it in the core triaxial clamping system after processing it into a cube; preferably, process the target core as per the dimension of 5 cm×5 cm×5 cm, and pay attention to the flatness of each end face during processing so as to load the applied stress to each end face of rock sample uniformly and avoid stress concentration;

(4) Inspect the connectivity and air tightness of the remaining parts of the testing device for sensitivity damage of core permeability tensor, and then enter the next step;

(5) Place the target rock sample on the core clamping panel at the lower part of z axis, operate the pressure loading control system to fix the target core on the core clamping panel, and then load the corresponding applied stresses in different directions according to the applied stresses of the first time step in three directions obtained in Step (2), carry out three-directional displacement under the stress state, and record the experimental monitoring data;

(6) According to the variable step lengths set in Step (2), carry out three-directional displacement of the second time step, the third time step, . . . and the time step i in an order of stress from small to large, and record the experimental monitoring data;

$$P_{x2} = P_{x1} + \Delta P_x \quad (14)$$

$$P_{y2} = P_{y1} + \Delta P_y \quad (15)$$

$$P_{z2} = P_{z1} + \Delta P_z \quad (16)$$

(7) According to the experimental monitoring data in Step (5) and Step (6), calculate the permeability value of target core in each direction in combination with the Equations (4)-(6);

(8) According to the permeability value in each direction, calculate the three-directional sensitivity damage rate of target core at each time step under the applied triaxial stress conditions as well as the maximum stress sensitivity damage rate of three-directional permeability for target core in combination with the Equations (7)-(12), in which the direction having the maximum damage rate of core permeability is that having the strongest stress sensitivity of core permeability.

In a specific embodiment, by taking a target core of 5 cm×5 cm×5 cm in a target reservoir for an example, the present invention is used for carrying out the stress sensitivity test of core permeability tensor.

Determine the original stress distribution of reservoir according to seismic interpretation of this target reservoir, logging information, ground stress test data and other related data, and decompose the stress on target core into the vertical stress $P_z$ and two horizontal stresses $P_x$ and $P_y$ orthogonal to the vertical stress, namely 20 MPa, 16 MPa and 15 MPa. The original pore pressure of reservoir is 8 MPa, the pore pressure is 4 MPa when the oil reservoir is abandoned, the side length of target core is 5 cm, the three-directional displacement rate is 1 ml/min, and the viscosity of experimental fluid is 1 MPa·s.

According to the experimental requirements, the number N of time steps is set as 2, and the variable step length of pressure in each axial direction is as follows:

$$\Delta P_x = \Delta P_y = \Delta P_z = \frac{P_1 - P_i}{N} = \frac{8 - 4}{2} = 2 \text{ Mpa} \quad (17)$$

The applied triaxial stress at each time step is shown as follows:

TABLE 1

Applied triaxial stress at each time step

| Direction | Pressure at the first time step (MPa) | Pressure at the second time step (MPa) | Pressure at the third time step (MPa) |
|---|---|---|---|
| $P_x$ | 12 | 14 | 16 |
| $P_y$ | 8 | 10 | 12 |
| $P_z$ | 7 | 9 | 11 |

TABLE 2

Inlet and outlet pressure of each time step in three directions

| Direction | Pressure at the first time step (MPa) | Pressure at the second time step (MPa) | Pressure at the third time step (MPa) |
|---|---|---|---|
| $P_{x-in}$ | 0.01312336 | 0.01773049 | 0.02178649 |
| $P_{x-out}$ | 0 | 0 | 0 |
| $P_{y-in}$ | 0.01692047 | 0.01915708 | 0.02150537 |
| $P_{y-out}$ | 0 | 0 | 0 |
| $P_{z-in}$ | 0.09523809 | 0.10101010 | 0.114942529 |
| $P_{z-out}$ | 0 | 0 | 0 |

Through the calculation of inlet and outlet pressure in three directions at each time step, the three-direction permeability at each time step is shown in Table 3:

TABLE 3

Three-directional permeability at each time step

| Direction | Permeability at the first time step (mD) | Permeability at the second time step (mD) | Permeability at the third time step (mD) |
|---|---|---|---|
| $P_x$ | 254 | 188 | 153 |
| $P_y$ | 197 | 174 | 155 |
| $P_z$ | 35 | 33 | 29 |

Through the calculation of three-directional permeability at each time step, the sensitivity damage rate of three-directional permeability for the target core is shown in Table 4:

TABLE 4

Sensitivity damage rate of three-directional permeability for the target core

| Direction | Damage rate at the first time step and the second time step (%) | Damage rate at the second time step and the third time step (%) |
|---|---|---|
| $P_x$ | 25.98 | 39.76 |
| $P_y$ | 11.67 | 21.31 |
| $P_z$ | 5.71 | 17.14 |

Seen from Table 4, the maximum sensitivity damage rate of permeability is 39.76% in the x direction, 21.31% in the y direction and 17.14% in the z direction. The permeability along the x direction is the largest, and the sensitivity damage rate is also the largest. The x direction is the direction having the strongest stress sensitivity of the target core permeability.

In summary, the present invention can measure the permeability tensor loss of core in different conditions (acid, alkali, salt, water, rate and stress) under the triaxial stress state through calculation, determine the permeability sensitivity in each direction, and provide strong basis for the formulation of oil and gas field development plans. Compared with the prior art, the present invention has significant progress.

The above are not intended to limit the present invention in any form. Although the present invention has been disclosed as above with embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

What is claimed is:

1. An evaluation method for sensitivity damage of core permeability tensor of a cubic core taken from a target reservoir, characterized in that the evaluation is carried out using the testing device for sensitivity damage of core permeability tensor, a testing device for sensitivity damage of core permeability tensor comprises a core triaxial clamping system, a three-dimensional and three-directional displacement system, a back pressure system, a pressure monitoring system, a temperature simulation system, and a gas-liquid recovery system;

The core triaxial clamping system comprises six core clamping panels and three sets of pressure loading systems, the six core clamping panels are used to clamp the six sides of the cubic core, and the two adjacent core clamping panels are sealed by a seal assembly; each set of pressure loading system comprises two oil pumps, two hydraulic transmission rods, and a control system; the oil pump is connected with the hydraulic transmission rod, and the two hydraulic transmission rods of the same set of pressure loading system are respectively connected with the relative two core clamping panels, and the control system is used to control the two hydraulic transmission rods of the same set of pressure loading system to apply equal and opposite pressure loads on two opposite end faces of the target core;

The three-dimensional and three-directional displacement system is connected with the core triaxial clamping system for three-dimensional and three-directional displacement of the cubic core; the back pressure system is connected to the core triaxial clamping system for applying back pressure to the cubic core; the pressure monitoring system is used to monitor a fluid pressure at an inlet end and at an outlet end of the cubic core, the back pressure at the outlet end of the cubic core, and a pressure load applied to the cubic core in each direction; the temperature simulation system is used to simulate the formation temperature conditions; and the gas-liquid recovery system is used to recover waste liquid and waste gas generated during a test;

The evaluation method for sensitivity damage of core permeability tensor comprises the following steps:

S1: Collect geological data about the target reservoir, obtain a stress distribution of the target reservoir, and decompose the stress distribution on the core into vertical stress $P_z$ and two horizontal stresses $P_x$ and $P_y$ orthogonal to the vertical stress;

S2: Obtain a target core of the target reservoir, install the target core in the core triaxial clamping system after processing the target core into a cube, and test connectivity and air tightness of the device after installation;

S3: Based on the three-directional displacement of the target core, carry out a sensitivity damage test, and record pressure and flow data monitored in the displacement process in each direction; wherein the sensitivity damage test includes an acid sensitivity test, an alkali sensitivity test, a salt sensitivity test, a water sensitivity test, a rate sensitivity test or a stress sensitivity test, or a combination of them;

S4: Calculate a permeability value of the target core in each direction according to the pressure and flow data, and calculate a sensitivity damage rate in each direction according to the permeability value in each direction, where the direction corresponding to the maximum sensitivity damage rate is the direction having the strongest permeability sensitivity of the target core;

The permeability value in each direction is calculated according to the following equations:

$$K_{xi} = \frac{Q_{xi} \times \mu \times L}{A \times (P_{xi-in} - P_{xi-out})} \quad (4)$$

-continued $$K_{yi} = \frac{Q_{yi} \times \mu \times L}{A \times (P_{yi-in} - P_{yi-out})} \quad (5)$$

$$K_{zi} = \frac{Q_{zi} \times \mu \times L}{A \times (P_{zi-in} - P_{zi-out})} \quad (6)$$

Where, $K_{xi}$, $K_{yi}$ and $K_{zi}$ are respectively the permeability values of the target core under a time step i in x, y and z directions; $Q_{xi}$, $Q_{yi}$ and $Q_{zi}$ are respectively flow rates under the time step i in x, y and z directions; μ is a viscosity of displacement fluid; L is the length of the target core; A is the cross sectional area of the target core; $P_{xi-in}$, $P_{yi-in}$ and $P_{zi-in}$ are respectively inlet pressures under the time step i in x, y and z directions; $P_{xi-out}$, $P_{yi-out}$ and $P_{zi-out}$ are respectively outlet pressures under the time step i in x, y and z directions;

The sensitivity damage rate in each direction is calculated according to the following equations:

$$D_{x(i-1)} = \frac{K_{x1} - K_{xi}}{K_{x1}} \times 100\% \quad (7)$$

$$D_{y(i-1)} = \frac{K_{y1} - K_{yi}}{K_{y1}} \times 100\% \quad (8)$$

$$D_{z(i-1)} = \frac{K_{z1} - K_{zi}}{K_{z1}} \times 100\% \quad (9)$$

Where, $D_{x(i-1)}$, $D_{y(i-1)}$ and $D_{z(i-1)}$ are respectively sensitivity damage rates of target core in x, y and z directions after a time step 1 changes into the time step i;

The maximum sensitivity damage rates in each direction are calculated according to the following equations:

$$D_{xmax} = \max(D_{x1}, D_{x2}, \ldots D_{x(n-1)}) \quad (10)$$

$$D_{ymax} = \max(D_{y1}, D_{y2}, \ldots D_{y(n-1)}) \quad (11)$$

$$D_{zmax} = \max(D_{z1}, D_{z2}, \ldots D_{z(n-1)}) \quad (12)$$

Where, $D_{xmax}$, $D_{ymax}$ and $D_{zmax}$ are respectively the maximum sensitivity damage rates in x, y and z directions; $D_{x1}$, $D_{x2}$ and $D_{x(n-1)}$ are respectively the sensitivity damage rates in x direction after the time step 1 changes into a time step 2, into a time step 3 and into a time step n; $D_{y1}$, $D_{y2}$ and $D_{y(n-1)}$ are respectively the sensitivity damage rates in y direction after the time step 1 changes into the time step 2, into the time step 3 and into the time step n; $D_{z1}$, $D_{z2}$ and $D_{z(n-1)}$ are respectively the sensitivity damage rates in z direction after the time step 1 changes into the time step 2, into the time step 3 and into the time step n.

2. The evaluation method for sensitivity damage of core permeability tensor according to claim 1, wherein the center of the core clamping panel is provided with a fluid channel that runs through the core clamping panel, the inner surface of the core clamping panel is provided with a plurality of coaxial annular grooves with the center of the core clamping panel as the center, the annular grooves are connected through a linear groove, and the linear groove is connected with the fluid channel.

3. The evaluation method for sensitivity damage of core permeability tensor according to claim 2, wherein a plurality of linear grooves are arranged, which are distributed in a ring array on the core clamping panel with the center of the core clamping panel as the center.

4. The evaluation method for sensitivity damage of core permeability tensor according to claim 1, wherein, in the S3, when the acid sensitivity test is carried out, the target core is loaded with corresponding applied stress according to the triaxial stress obtained in the S1, and then injected with an experimental acid liquor which is 0.5-1.5 times as much as the pore volume; the three-dimensional and three-directional displacement is carried out after the target core reacts with the experimental acid liquor for 0.5 hours;

When the alkali sensitivity test, the salt sensitivity test or the water sensitivity test is carried out, the target core is loaded with corresponding applied stress according to the triaxial stress obtained in the S1, and then injected with a corresponding experimental fluid which is 10-15 times as much as the pore volume; the three-dimensional and three-directional displacement is carried out after the target core reacts with the experimental corresponding fluid for 12 hours.

5. The evaluation method for sensitivity damage of core permeability tensor according to claim 1, wherein, in the S3, when a rate sensitivity test is carried out, the target core is loaded with corresponding applied stress according to the triaxial stress obtained in step S1; different flow rates are set, and the three-dimensional and three-directional displacement is carried out in the order of flow rate from small to large.

6. The evaluation method for sensitivity damage of core permeability tensor according to claim 1, wherein, in the S3, when a stress sensitivity test is carried out, the method comprises the following sub-steps:

S31: Set the variable step lengths $\Delta P_x$, $\Delta P_y$ and $\Delta P_z$ of pressure in each direction;

S32: Determine the applied stress of the first time step in each direction, and use the applied stress of the first time step for the three-directional displacement;

S33: According to the variable step lengths of pressure set in the S31, successively carry out the three-directional displacement under the applied stresses of the second time step, the third time step, . . . and the time step i.

7. The evaluation method for sensitivity damage of core permeability tensor according to claim 6, wherein, in the S31, the variable step lengths of pressure in each direction are within 3-5 MPa.

8. The evaluation method for sensitivity damage of core permeability tensor according to claim 6, wherein, in the S32, the applied stress of the first time step in each direction is calculated according to the following equations:

$$P_{x1} = P_x - P_1 \quad (1)$$

$$P_{y1} = P_y - P_1 \quad (2)$$

$$P_{z1} = \rho g h - P_1 \quad (3)$$

Where, $P_{x1}$, $P_{y1}$ and $P_{z1}$ are respectively effective formation stresses of the target core under the first time step in x, y and z directions; $P_x$ and $P_y$ are respectively the original formation stresses of the target core in x and y directions; $P_1$ is the original pore pressure of reservoir; ρ is the target core density; g is the gravitational acceleration; and h is the buried depth of target core.

* * * * *